United States Patent [19]

Marx et al.

[11] 4,267,106
[45] May 12, 1981

[54] NEW PROCESS FOR THE PREPARATION 17β-HYDROXY-3-OXO-17α-PREGNENE AND PREGNADIENE-21-CARBOXYLIC ACID γ-LACTONES

[75] Inventors: Arthur F. Marx, Delft; Peter M. Smid, Bleiswijk; Pieter Vellekoop, The Hague, all of Netherlands

[73] Assignee: Gist Brocades N.V., Delft, Netherlands

[21] Appl. No.: 66,854

[22] Filed: Aug. 15, 1979

[30] Foreign Application Priority Data

Aug. 15, 1978 [GB] United Kingdom ............... 33384/78

[51] Int. Cl.³ .......................... C07J 71/00; C07J 73/00
[52] U.S. Cl. ............................ 260/239.57; 260/239.5; 260/239.55 R
[58] Field of Search .................................... 260/239.57

[56] References Cited

U.S. PATENT DOCUMENTS

| | | | |
|---|---|---|---|
| 3,382,239 | 5/1968 | Barton | 260/239.57 |
| 3,632,576 | 1/1972 | Lehmann et al. | 260/239.57 |
| 3,883,512 | 5/1975 | Stache et al. | 260/239.57 |
| 3,900,467 | 8/1975 | Irmscher et al. | 260/239.57 |

*Primary Examiner*—Elbert L. Roberts

*Attorney, Agent, or Firm*—Robert E. Burns; Emmanuel J. Lobato; Bruce L. Adams

[57] ABSTRACT

A process is disclosed for the preparation of 17β-hydroxy-3-oxo-17α-pregn-4-ene-21-carboxylic acid γ-lactone and 17β-hydroxy-3-oxo-17α-pregna-4,6-diene-21-carboxylic acid γ-lactone of the formula:

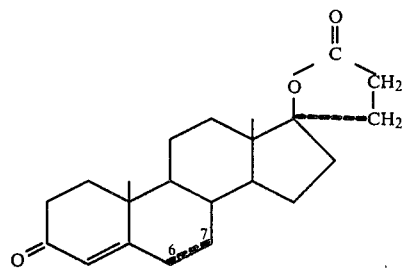

wherein the dotted line between the 6–7 positions indicates an optional double bond, which is present in the latter compound, by reacting an androst-5-ene-17-one derivative with an organo-phosphorus compound. These lactones are valuable intermediates in the synthesis of spironolactone.

14 Claims, No Drawings

NEW PROCESS FOR THE PREPARATION 17β-HYDROXY-3-OXO-17α-PREGNENE AND PREGNADIENE-21-CARBOXYLIC ACID γ-LACTONES

BACKGROUND OF THE INVENTION

This invention relates to a new process for the preparation of valuable intermediates in the synthesis of spironolactone.

More particularly, the invention relates to a process for the preparation of 17β-hydroxyl-3-oxo-17α-pregn-4-ene-21-carboxylic acid γ-lactone and 17β-hydroxy-3-oxo-17α-pregna-4,6-diene-21-carboxylic acid γ-lactone of the formula:

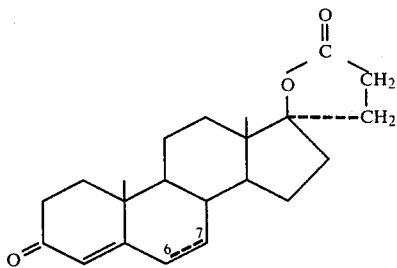

wherein the dotted line between the 6–7 positions indicates the additional double bond of the latter compound.

The $\Delta^6$-derivative of formula I can be readily reacted in a manner known per se with thioacetic acid (e.g. according to the procedure described in British Pat. No. 889310) to obtain spironolactone of the formula:

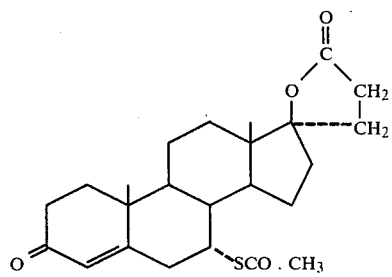

which is a commercially available, therapeutically active compound having outstanding diuretic and antihypertensive properties.

Previously the synthesis of steroid γ-lactones such as the compounds represented by formula I starting from readily available materials, for example, dehydroepiandrosterone (hereinafter abbreviated to DHA) or androst-4-ene-3,17-dione (hereinafter abbreviated to AD), was a rather complicated process, particularly since several reaction steps were required for the formation of the γ-lactone ring, as disclosed for example, in U.S. Pat. No. 2,705,712. This reference discloses a process starting from e.g., DHA which is reacted with a metal derivative of acetylene to give the 17β-hydroxy-17α-acetylene derivative which, after reacting with a Grignard compound to form the corresponding Grignard derivative, followed by carbon dioxide addition, is converted into the corresponding 17α-hydroxy-17β-(3-propynoic acid) compound which, after catalytic hydrogenation and acidification, is converted into the 17α-hydroxy-17β-(3-propenoic acid) γ-lactone which, in turn, is catalytically hydrogenated to the 17α-hydroxy-17β-(3-propanoic acid) γ-lactone. In this compound the 3-hydroxy group must still be further oxidized to obtain the 3-oxo-$\Delta^4$ compound and further to the 3-oxo-$\Delta^{4,6}$- diene. Thus several steps are involved to build up the γ-lactone ring.

In another process, according to German Patent Applications Nos. 2,404,946 and 2,404,947, 3-hydroxy-17-oxo-androsta-3,5-diene, having the 3-hydroxy group protected, is converted into the 2',3' α-oxirane-2'-spiro-17-androst-4-en-3-one derivative which is treated with a dialkylmalonate in the presence of a base to form a 17α-hydroxy-17β-(alkoxycarbonylpropanic acid)γ-lactone. After decarboxylation the desired γ-lactone ring is obtained. This process also involves several steps to build up the γ-lactone ring.

Another example of a process to form spironolactone is disclosed in U.S. Pat. No. 4,057,542, according to which the 3-hydroxy group of a 17β-hydroxy-17α-acetylene derivative (cf. U.S. Pat. No. 2,705,712 cited hereinabove) is protected and the compound is treated with a lower alkylvinyl ether to form the 17β-(1-lower alkoxy-1-ethoxy)-17α-ethynyl compound, which is treated with alkyllithium or a Grignard compound and carbon dioxide to form the 17β-(1-lower alkoxy-1-ethoxy)-17α-(3-propynoic acid) which is converted into the 17β-hydroxy-17α-(3-propynoic acid) which, after catalytic hydrogenation and acidification, is converted into the 17β-hydroxyl-17α-(3-propanoic acid)γ-lactone.

Here again several steps are involved to build up the γ-lactone ring. The references cited above show only a part of all known routes to arrive at 17β-hydroxy-3-oxo-17α-pregn-4-ene-21-carboxylic acid γ-lactone, which always involve several steps.

SUMMARY OF THE INVENTION

The principal object of the present invention is the provision of an improved process for the preparation of 17β-hydroxy 3-oxo-17α-pregn-4-ene-21-carboxylic acid γ-lactone and 17β-hydroxy-3-oxo-17α-pregna-4,6-diene-21-carboxylic acid γ-lactone.

It now has been found that such a γ-lactone ring can be formed on certain androstenones in one single reaction step and in good yield, starting from readily available derivatives of DHA or AD, or even from DHA itself.

The new process of the invention for the preparation of the steroid γ-lactones of formula I comprises reacting an androst-5-ene-17-one derivative of the formula:

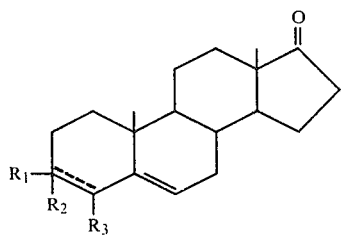

wherein (i) $R_1$ represents a group —$OR_4$ in which $R_4$ represents a hydrogen atom, an alkyl or alkoxyalkyl group or a group $$-\underset{\underset{OR_6}{|}}{CH}-R_5'$$

wherein $R_5$ represents a hydrogen atom or an alkyl group and $R_6$ represents an alkyl group, or $R_5$ and $R_6$ together with the carbon and oxygen atoms to which they are attached represent a 5- or 6-membered heterocyclic group, and $R_2$ and $R_3$ each represent a hydrogen atom; or (ii) $R_1$ and $R_2$ are the same or different and each represents a group $-OR_{4'}$, wherein $R_{4'}$ represents an alkyl group, or $R_1$ and $R_2$ together represent an alkylenedioxy group having 2 or 3 carbon atoms in the alkylene moiety, and $R_3$ represents a hydrogen atom, or (iii) $R_1$ represents a group $-OR_{4'}$ or a group $$-N\begin{matrix}R_7\\ \\R_8\end{matrix}$$

wherein $R_7$ and $R_8$ are the same or different and each represents an alkyl group, or $R_7$ and $R_8$ together with the nitrogen atom to which they are attached represent a 5- or 6-membered heterocyclic group, which may contain a further hetero atom in the ring, and $R_2$ and $R_3$ together represent an additional bond in the 3-4 position with an organo-phosphorus compound of the formula:

$$\underset{R}{\overset{R}{\diagdown}}\overset{O}{\overset{\|}{P}}-O-CH_2-CH=CH_2 \qquad IV$$

wherein

R represents a group $-OR'$, in which $R'$ represents an alkyl group, or R represents a group $-N(R'')_2$ in which $R''$ represents an alkyl group or $-N(R'')_2$ represents a 5- or 6-membered heterocyclic group, which may contain a further hetero atom in the ring.

in an organic medium at a temperature between $-90°$ and $+50°$ C. in the presence of a strong base to obtain a corresponding γ-lactone of the formula:

wherein $R_1$, $R_2$ and $R_3$ are as hereinbefore defined, and converting by methods known per se the compound thus obtained into the 3-oxo-pregn-4-ene-21-carboxylic acid γ-lactone or the 3-oxo-pregna-4,6-diene-21-carboxylic acid γ-lactone of formula I.

DESCRIPTION OF THE INVENTION

By the term "alkyl" as used in this specification is meant straight- or branched-chain alkyl groups containing up to six carbon atoms. Examples of suitable alkyl groups are methyl, ethyl, propyl and butyl groups. By the term "methods known per se" is meant methods heretofore used or described in the literature.

Particularly suitable starting materials of formula III are 3-methoxy- or 3-ethoxy-, 3-propoxy- or 3-butoxy-androsta-3,5-dien-17-one, 3β(2'-tetrahydropyranyloxy)-androst-5-en-17-one, 3,3-ethylenedioxy-androst-5-en-17-one, 3-(1'-pyrrolidinyl)-androsta-3,5-dien-17-one and 3,5-dien-17-one and 3-(N-morpholinyl)-androsta-3,5-dien-17-one.

Particularly suitable organo-phosphorus compounds of formula IV are allyl phosphate bis-dimethyl- and bis-diethylamide, allyl dimethyl phosphate and allyl diethyl phosphate.

The reaction between the androstenone derivatives of formula III and the organo-phosphorus compounds of formula IV is carried out in an organic medium; suitable solvents are, for example, ethers such as tetrahydrofuran, diethyl ether, 1,2-dimethoxyethane and dioxane, aromatic hydrocarbons such as benzene, toluene, xylene, naphthalene, and aliphatic hydrocarbons such as pentane, hexane and cyclohexane, tertiary amines such as triethylamine and mixtures thereof.

During the reaction the temperature is preferably maintained between $-70°$ and $0°$ C.

Suitable strong bases necessarily present in the reaction mixture are, for example, alkyl- or aryl-lithium compounds; examples of suitable bases are n-butyllithium, t-butyllithium, methyllithium and phenyllithium. Preferably n-butyllithium is used.

The organo-phosphorus compound of formula IV is activated by means of the strong base in the reaction medium and the activated form then reacts in situ with the androstenone derivative of formula III. The activation of such organo-phosphorus compounds by means of strong bases has been described by G. Sturz, C.R. Acad. Sc. Paris, t. 277 (1973) 395; who also has disclosed the formation of γ-lactones from the phosphorus compound and an aldehyde; this reaction has been exemplified for other aldehydes and for ketones in a later publication of G. Sturtz et al., Tetrahedron Letters 1 (1976) 47–50.

The γ-lactones of formula V can be converted by methods known per se into the corresponding 3-keto-$\Delta^4$ and 3-keto-$\Delta^{4,6}$ derivatives of formula I.

The γ-lactones of formula V wherein $R_1$ represents a group $-OR_{4'}$ (wherein $R_{4'}$ is as hereinbefore defined) and $R_2$ and $R_3$ together represent an additional bond in the 3-4 position, or wherein $R_1$ and $R_2$ are the same or different and each represents a group $-OR_{4'}$ (wherein $R_{4'}$ is as hereinbefore defined), or $R_1$ and $R_2$ together represent an alkylidenedioxy group, and $R_3$ represents a hydrogen atom, can be converted by simple hydrolysis into the 3-keto-$\Delta^4$ derivative of formula I.

The 3-keto-$\Delta^4$ compound thus obtained can be converted into the corresponding 3-keto-$\Delta^{4,6}$ derivative of formula I by heating with chloranil in a suitable organic solvent such as t-butanol or xylene.

Alternatively, the γ-lactones of formula V, wherein $R_1$ represents a group $-OR_{4'}$ (wherein $R_{4'}$ is as hereinbefore defined) and $R_2$ and $R_3$ together represent an additional double bond in the 3-4 position, can be converted directly into the 3-keto-$\Delta^{4,6}$ compound of formula I. This conversion whereby hydrolysis and introduction of a double bond between the 6–7 positions are combined in one single reaction step, can be effected in manner known per se by reacting such a γ-lactone of formula V at room temperature with 2,3-dichloro-5,6-dicyano-benzoquinone (DDQ) or with chloranil in, for example, an acetone and water mixture (95/5/; v/v).

As the aforesaid γ-lactones can be converted quite conveniently by means of DDQ or chloranil directly into the 3-keto-Δ$^{4,6}$ compound of formula I, which is, as explained above, a valuable intermediate in the process of preparing spironolactone, the corresponding 3-enol ethers of AD (i.e. the compounds of formula III wherein $R_1$, $R_2$ and $R_3$ are as defined in the preceding paragraph) are particularly preferred starting materials in the process of the invention.

On the other hand, when other starting materials are used, the conversion of the resulting γ-lactones of formula V into the 3-keto-Δ$^{4,6}$ derivative of formula I always necessitates at least one additional reaction step, viz. oxidation and/or introduction of the double bond in 6–7 position, after the actual hydrolysis has been carried out.

Upon hydrolysis of a γ-lactone of formula V, wherein $R_1$ represents an alkoxyalkyl group or a group $$-\underset{\underset{OR_6}{|}}{CH}-R_5$$

(wherein $R_5$ and $R_6$ are as hereinbefore defined) and $R_2$ and $R_3$ each represent a hydrogen atom, in the manner hereinbefore described, there is obtained the corresponding γ-lactone of formula V wherein $R_1$ represents a hydroxy group, i.e. 3β,17β-dihydroxy-17α-pregn-5-ene-21-carboxylic acid γ-lactone.

The same compound is obtained directly when the process of the invention is effected with the androstenone of formula III wherein $R_1$ represents a hydroxy group and $R_2$ and $R_3$ each represent a hydrogen atom, i.e. with dehydroepiandrosterone (DHA) itself.

The 3β,17β-dihydroxy-17α-pregn-5-ene-21-carboxylic acid γ-lactone thus obtained can be converted into the corresponding 3-keto-Δ$^4$ derivative of formula I by means of an Oppenauer oxidation. This reaction can be effected by means of an aluminum-catalyzed hydrogen exchange, for example, by means of aluminum triisopropylate, between the alcoholic function and an accepting carbonyl compound, such as cyclohexanone or N-methylpiperidione, in an inert organic solvent, e.g. toluene, with heating of the reaction mixture.

The γ-lactones of formula V wherein $R_1$ represents a group

(wherein $R_7$ and $R_8$ are as hereinbefore defined) can be converted into the 3-keto-Δ$^4$ compound of formula I by heating the γ-lactone in an acetic acid/sodium acetate mixture or a 96% ethanol solution.

The starting materials of formula III can be easily obtained in manner known per se and in very good yields from androst-4-ene-3,17-dione (AD) or from dehydroepiandrosterone (DHA). AD is nowadays readily available in large quantities from fermentative side-chain degradation of various sterols. DHA can be obtained by similar processes but is still mainly prepared on a very large scale by chemical conversion of diosgenin, which product is obtained from the root-stocks of Dioscorea varieties.

The starting materials of formula III, wherein $R_1$ represents a group —$OR_4'$ (wherein $R_4'$ is as hereinbefore defined) and $R_2$ and $R_3$ together represent an additional bond between the 3–4 positions, can be prepared from AD by acid-catalyzed reaction with orthoformates of the formula $CH(OR_4')_3$—$R_4'$ being as hereinbefore defined, at room temperature.

The starting materials of formula III, wherein $R_1$ represents a group —$OR_4$, and $R_4$ represents an alkyl group and $R_2$ and $R_3$ each represent a hydrogen atom, can be obtained by reaction of DHA with the corresponding alkyl halide in the presence of a base.

The starting materials of formula III, wherein $R_1$ represents a group

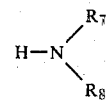

(wherein $R_7$ and $R_8$ are as hereinbefore defined) and $R_2$ and $R_3$ together represent an additional bond between the 3–4 positions, can be prepared from AD and the corresponding amine

with or without a catalyst, by azeotropic removal of water.

The compound of formula III wherein $R_1$ represents the 1-pyrrolidinyl group and $R_2$ and $R_3$ together represent an additional bond between the 3–4 positions, can also be prepared very conveniently by addition of pyrrolidine to a hot solution of AD in methanol, followed by immediate cooling.

The starting materials of formula III wherein $R_1$ and $R_2$ each represents a group —$OR_4'$ (wherein $R_4'$ is as hereinbefore defined), or $R_1$ and $R_2$ together represent an alkylenedioxy group, and $R_3$ represents a hydrogen atom, can be prepared from AD by first protecting the 17-keto group, for example, by converting AD into the corresponding 17-cyanohydrin. This cyanohydrin compound is then reacted with the desired alcohol, such as ethanol or ethylene glycol, in the presence of an acid catalyst, for example p-toluenesulphonic acid, followed by removal of the protecting group of the 17-moiety by heating in the presence of a base, such as pyridine.

The starting materials of formula III, wherein $R_1$ represents a group

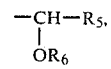

wherein $R_5$ represents an alkyl group and $R_6$ is as hereinbefore defined, or $R_5$ and $R_6$ together represent an alkylene group forming part of a 5- or 6-membered heterocyclic group, and $R_2$ and $R_3$ each represent a hydrogen atom, can be prepared by heating DHA under acid catalysis with an enol ether of the formula

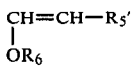

wherein $R_{5'}$ represents a hydrogen atom, viz. in the case when $R_5$ is a methyl group, or an alkyl group having one carbon atom less than $R_5$, and $R_6$ is as hereinbefore defined, or $R_5$ and $R_6$ together with the carbon and oxygen atoms to which they are attached represent a 5- or 6-membered heterocyclic group.

The starting materials of formula III, wherein $R_1$ represents a group

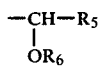

(wherein $R_5$ and $R_6$ are as hereinbefore defined) and $R_2$ and $R_3$ each represent a hydrogen atom, can be prepared in similar manner by reaction of DHA with an acetal of the formula

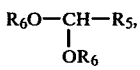

wherein $R_5$ and $R_6$ are as hereinbefore defined.

The organo-phosphorus compounds of formula IV can be prepared in a manner known per se by reaction of a corresponding phosphorochloridate of the formula:

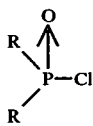   VI (wherein R is as hereinbefore defined) with allyl alcohol in the presence of a base, such as pyridine, or with an alkali metal prop-2-en-1-olate, e.g. sodium prop-2-en-1-olate, at temperatures below 50° C.

The phosphorochloridates of formula VI can be prepared by reaction of an alcohol R'OH (wherein R' is as hereinbefore defined) or an amine NH(R")$_2$ (wherein R" is as hereinbefore defined) with POCl$_3$ at temperatures below 0° C., or by reaction of a compound of the formula:

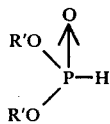   VII (wherein R' is as hereinbefore defined) with tetrachloromethane in the presence of a base, preferably triethylamine.

The following Examples illustrate the best mode currently contemplated for carrying out the present invention, but must not be construed as limiting the invention in any manner.

EXAMPLE I (a) Under a constant stream of dry nitrogen gas a solution of 334 mg (1.7 mmoles) of allyl diethylphosphate in 2.5 ml of tetrahydrofuran was added dropwise and with stirring to a solution of 2.5 ml of a 1.3 M solution of n-butyllithium in hexane (3.25 mmoles) at a temperature between −45° C. and −50° C. After 1 hour a solution of 155 mg (0.51 mmole) of 3-methoxy-androsta-3,5-dien-17-one in 1 ml of tetrahydrofuran was added. After another 40 minutes water was added, the cooling bath was removed and the organic layer was washed with methyl isobutyl ketone and some more water. The aqueous layer was removed and the organic layer was washed with water and evaporated in vacuo. After crystallization of the residue from heptane, there were obtained 150 mg (yield 83%) of crystalline 3-methoxy-17β-hydroxy-17α-pregna-3,5-diene-21-carboxylic acid γ-lactone; m.p. 226°–232° C. (decomp.).

IR (CHCl$_3$): 1765, 1655, 1630, 1170 cm$^{-1}$.

(b) A solution of 4.45 g (19.6 mmoles) of 2,3-dichloro-5,6-dicyano-benzoquinone (hereinafter abbreviated to DDQ) in 50 ml of a mixture of acetone and water (95/5; v/v) was added within 2 minutes to a stirred suspension of 6.34 g (17.8 mmoles) of 3-methoxy-17β-hydroxy-17α-pregna-3,5-diene-21-carboxylic acid γ-lactone, prepared according to the procedure described in (a), in 150 ml of the same acetone and water mixture. After stirring for another 30 minutes, the reaction mixture was concentrated. Toluene was added to the residue and some insoluble material was filtered off. The aqueous layer was separated and the toluene removed in vacuo. The residue was crystallized from methanol. After washing and drying, there were obtained 2.76 g (yield 46%) of white, crystalline 17β-hydroxy-3-oxo-17α-pregna-4,6-diene-21-carboxylic acid γ-lactone; m.p. 163.5°–165° C.

IR (CHCL$_3$): 1760, 1650, 1620, 1590, 1180, 1020 cm$^{-1}$.

EXAMPLE II

A suspension of 10 g of 3-methoxy-17β-hydroxy-17α-pregna-3,5-diene-21-carboxylic acid γ-lactone, prepared according to the procedure described in Example I(a), in 100 ml of a mixture of acetone and water (95/5; v/v) and 7.0 g of chloranil was refluxed for 30 minutes. The reaction mixture was cooled and the acetone was removed in vacuo. The residue was dissolved in 200 ml of toluene and the solution was washed twice with 50 ml of a 1 N sodium hydroxide solution in water and three times with 100 ml of water. The organic solvent was removed in vacuo. The residue obtained (10.4 g) was crystallized from ethyl acetate. There were obtained 6.3 g (yield 66%) of practically white crystalline 17β-hydroxy-3-oxo-17α-pregna-4,6-diene-21-carboxylic acid γ-lactone; m.p. 163°–164° C.

Concentration of the mother liquors resulted in another 1.5 g (yield 16%) of the same product.

EXAMPLE III

A solution of 1.0 g (5.2 mmoles) of allylphosphate bis-dimethylamide in 6 ml of tetrahydrofuran was slowly added at −50° C. to a mixture of 8 ml of a 1.3 M solution of n-butyllithium in hexane (10.4 mmoles) and 5 ml of dry tetrahydrofuran under a constant stream of dry nitrogen gas. The mixture was stirred for 90 minutes, then cooled to −70° C., and a solution of 1.3 g (4.1 mmoles) of 3-ethoxyandrosta-3,5-dien-17-one in 8 ml of dry tetrahydrofuran was added. Stirring was continued for 90 minutes at −70° C. and then 0.5 ml of water in 1 ml of tetrahydrofuran was added and the cooling was discontinued. The temperature was allowed to rise to 20° C. and then methyl isobutyl ketone and water were added. The organic layer was separated and washed twice with water; the remaining aqueous layer was washed with methyl isobutyl ketone and the combined organic layers were concentrated after addition of one drop of pyridine. There were obtained 1.12 g of a white solid.

This product was dissolved in an acetone and water mixture (95/5; v/v) and then reacted with DDQ. After the usual working-up procedure and chromatography on a silica gel column (eluent toluene with 2% of acetone), there were isolated 300 mg (yield 22%) of 17$\beta$-hydroxy-3-oxo-17$\alpha$-pregna-4,6-diene-21-carboxylic acid $\gamma$-lactone; m.p. 146°–150° C.

IR (CHCl$_3$): 1765, 1660, 1621, 1588, 1172, 1020 cm$^{-1}$.

EXAMPLE IV

To 3 ml of tetrahydrofuran cooled to −40° C. were added 4 ml of a 1.3 M solution of n-butyllithium in hexane (5.2 mmoles) under a constant stream of dry nitrogen gas. After cooling to −50° C., a solution of 0.67 g (3.5 mmoles) of allylphosphate bis-dimethylamide in 3.5 ml of tetrahydrofuran was added with stirring. The stirring was continued for another 105 minutes at −45° C. and then a solution of 314 mg (1 mmole) of 3-ethoxy-androsta-3,5-dien-17-one in 4 ml of tetrahydrofuran was added dropwise at a temperature of −60° C., and the mixture was stirred for another 105 minutes. After addition of 0.5 ml of water in 1 ml of tetrahydrofuran, the solvent was removed in vacuo and the residue taken up in toluene. The organic layer was washed twice with water and the toluene was removed in vacuo. The residual oil was dissolved in 5 ml of acetone and 50 mg of p-toluenesulphonic acid were added. After stirring for 5 hours the solvent was removed in vacuo and the residue chromatographed on a silica gel column. After crystallization of the product from methanol, there were obtained 174 mg (yield 51%) of white, crystalline 17$\beta$-hydroxy-3-oxo-17$\alpha$-pregn-4-ene-21-carboxylic acid $\gamma$-lactone; m.p. 148°–150° C.

IR(CHCl$_3$): 1765, 1660, 1610, 1171 cm$^{-1}$.

EXAMPLE V

To a mixture of 10 ml of a 1.25 M methyllithium solution in diethyl ether, 3 ml of tetramethylethylenediamine and 4 ml of tetrahydrofuran there was added dropwise and with stirring a solution of 1.61 g (6.5 mmoles) of allylphosphate bis-diethtylamide in 1 ml of tetrahydrofuran at a temperature of −40° C. and under a nitrogen atmosphere. Stirring was continued for another 5 minutes and then a solution of 0.97 g (3.2 mmoles) of 3-methoxy-androsta-3,5-dien-17-one in 8 ml of tetrahydrofuran was added. After hydrolysis with methanol and water, the usual working-up procedure and column chromatography, there were obtained 228 mg (yield 20%) of 17$\beta$-hydroxy-3-oxo-17$\alpha$-pregn-4-ene-21-carboxylic acid $\gamma$-lactone.

EXAMPLE VI

A 0.8 M solution of n-butyllithium in hexane was diluted with 10 ml of freshly distilled tetrahydrofuran at −50° C. and under a constant stream of dry nitrogen gas. Then a mixture of 2.7 g of allylphosphate bis-dimethylamide and 5 ml of tetrahydrofuran was added. After stirring for 50 minutes at −50° C., a suspension of 1.0 g of 3-(1-pyrrolidinyl)androsta-3,5-dien-17-one in 25 ml of dry tetrahydrofuran was added and the mixture was stirred for another 30 minutes. After hydrolysis with a methanol and water mixture and addition of toluene and 1.25 ml of acetic acid, the mixture was shaken very thoroughly. The aqueous layer was extracted twice with toluene and the combined organic layers were washed twice with 20 ml portions of water and then concentrated. There was obtained 1.23 g of a solid.

700 mg of this product was hydrolysed by refluxing for 1 hour with 11.5 ml of methanol, 2.7 ml of water, 1.05 g of sodium acetate and 1.1 ml of acetic acid. After addition of water, extraction with toluene, and removal of the organic solvents, a solid was obtained which was chromatographed on silica gel. There were obtained 294 mg (yield 52%) of 17$\beta$-hydroxy-3-oxo-17$\alpha$-pregn-4-ene-21-carboxylic acid $\gamma$-lactone; m.p. 149°–151° C.

EXAMPLE VII (a) Following the procedure of Example I, 728 mg (2.53 mmoles) of dehydroepiandrosterone were converted into 436 mg (yield 50%) of 3$\beta$,17$\beta$-dihydroxy-17$\alpha$-pregn-5-ene-21-carboxylic acid $\gamma$-lactone; m.p. 183°–190° C.

IR (CHCl$_3$): about 3615, about 1765, 1179, 1047 and 1020 cm$^{-1}$.

(b) A mixture of 377 mg (1.1 mmole) of the product of (a), 13 ml of dry toluene, 1.7 ml of N-methylpiperidinone and 0.33 g (1.62 mmole) of aluminium triisopropylate was refluxed during 5.25 hours. After cooling, the reaction mixture was poured into ice-water and the solution was acidified with concentrated hydrochloric acid (pH 1.5). After separation of the aqueous layer and extraction with toluene, the combined organic layers were washed until neutral. After evaporation of the solvent, the residue was chromatographed on silica gel. There were obtained 257 mg (yield 68%) of crystals, which were recrystallized from methanol. This resulted in 80 mg of 17$\beta$-hydroxy-3-oxo-17$\alpha$-pregn-4-ene-21-carboxylic acid $\gamma$-lactone; m.p. 149.5°–151° C.

EXAMPLE VIII (a) A solution of 8.3 mg (33.4 mmoles) of allylphosphate bis-diethylamide in 10 ml of toluene was added dropwise with stirring to 40 ml of a 1.6 M solution of n-butyllithium in toluene at a temperature below −45° C. Stirring was continued for another 2 hours at −45° C. Then a solution of 3.3 g (10 mmoles) of 3,3-ethylenedioxy-androst-5-en-17-one in 40 ml of toluene was added over a period of 10 minutes at −45° C. The stirring was continued for another hour at temperatures between −40° and −50° C. The reaction mixture was quenched with 5 ml of methanol and diluted with water. The organic layer was separated and washed twice with water. The solvent was removed in vacuo and the residue crystallized from methanol. There were obtained 2.3 g (yield 60%) of 3,3-ethylenedioxy-17$\beta$-hydroxy-17$\alpha$-pregn-5-ene-21-carboxylic acid $\gamma$-lactone; m.p. 221°–223° C.

Upon concentration of the mother liquor there were obtained another 510 mg (yield 13%) of white crystals of the same product.

IR (CHCl$_3$): 1764, about 1670, 1112, 1100 and 1025 cm$^{-1}$.

(b) 386 mg (1 mmole) of the product of (a) were suspended in a solution of 5 ml of acetone, 0.2 ml of water and 50 mg of p-toluenesulphonic acid. After stirring for 75 minutes at room temperature the solid was dissolved completely. Stirring was continued for another 19 hours and then 0.05 ml of pyridine and 17 ml of water were added. The crystalline precipitate was collected by filtration and dried. There were obtained 190 mg (yield 56%) of 17$\beta$-hydroxy-3-oxo-17$\alpha$-pregn-4-ene-21-carboxylic acid $\gamma$-lactone; m.p. 148°–149.5° C. (methanol).

EXAMPLE IX (a) Following the procedure of Example I, 8.27 g (33.4 mmoles) of allylphosphate bis-diethylamide in 10 ml of toluene were added with stirring to 40 ml of a 1.6 M solution of n-butyllithium in toluene at a temperature below −45° C. The mixture was stirred for another 2 hours at −60° C. and then 3.72 g (10 mmoles) of 3$\beta$-(2'-tetrahydropyranyloxy)androst-5-en-17-one in 25 ml of toluene were added at −45° C. Stirring was continued for a further hour at a temperature between −40° and −50° C. and then the reaction mixture was quenched with 5 ml of methanol. Addition of water, working-up of the reaction mixture and crystallization of the product from methanol resulted in 2.6 g (yield 61%) of 3$\beta$-(2'-tetrahydropyranyloxy)-17$\beta$-hydroxy-17$\alpha$-pregn-5-ene-21-carboxylic acid $\gamma$-lactone; m.p. 182.5°–184.5° C.

IR (CHCl$_3$): 1765, 1132, 1075, 1030–1020 cm$^{-1}$.

(b) 428 mg (1 mmole) of the product of (a) in 5 ml of acetone, 0.2 ml of water and a trace of p-toluenesulphonic acid was stirred for 19 hours. After the usual working-up procedure there were obtained 180 mg (yield 52%) of 3$\beta$,17$\beta$-dihydroxy-17$\alpha$-pregn-5-ene-21-carboxylic acid $\gamma$-lactone.

Following the procedure of Example VIIb, this product could be converted into 17$\beta$-hydroxy-3-oxo-17$\alpha$-pregn-4-ene-21-carboxylic acid $\gamma$-lactone.

EXAMPLE X

Following the procedure of Example VIII 1.5 g (3.75 mmoles) of 3$\beta$-n-butoxyandrost-5-en-17-one were converted into 1.31 g (3.28 mmoles) of 3$\beta$-butoxy-17$\beta$-hydroxy-17$\alpha$-pregn-5-ene-21-carboxylic acid $\alpha$-lactone having, after crystallisation from methanol, a melting point of 92°–94° C. and IR absorptions (CHCl$_3$) of 1760 and 1090 cm$^{-1}$.

17$\beta$-Hydroxy-3-oxo-b 17$\alpha$-pregn-4-ene-21-carboxylic acid $\gamma$-lactone was prepared therefrom according to the method of Example VIIb.

EXAMPLE XI

Following the procedure of Example VI 1.6 g (4.5 mmoles) of 3-(N-morpholinyl)-androsta-3,5-dien-17-one were converted into 0.87 g (2.21 mmoles) of 3-(N-morpholinyl)-17$\beta$-hydroxy-17$\alpha$-pregna-3,5-diene-21-carboxylic acid $\gamma$-lactone which, after crystallisation from methanol, showed a melting point of 207°–210° C. and IR absorptions (CHCl$_3$) of 1760, 1638, 1608, 1119 and 1010 cm$^{-1}$.

After hydrolysis of 411 mg (1 mmole) of this product, according to the procedure of Example VI, 261 mg (0.76 mmole) of 17$\beta$-hydroxy-3-oxo-17$\alpha$-pregn-4-ene-21-carboxylic acid $\gamma$-lactone were obtained.

EXAMPLE XII

Following the procedure of Example VI 1.5 g (4.36 mmoles) of 3-(2-methoxyethoxy)-androsta-3,5-dien-17-one were converted into 0.88 g (2.2 mmoles) of 3-(2-methoyethoxy)-17$\beta$-hydroxy-17$\alpha$-pregna-3,5-diene-21-carboxylic acid $\gamma$-lactone as an oil, showing, after crystallisation from methanol, a melting point of 130°–137° C. and IR absorptions (CHCl$_3$) of 1760, 1652, 1625, 1168 and 1120 cm$^{-1}$.

After hydrolysis, according to the procedure of Example VIII, 17$\beta$-hydroxy-3-oxo-17$\alpha$-pregn-4-ene-21-carboxylic acid $\gamma$-lactone was obtained.

EXAMPLE XIII

Following the procedure of Example VI 1.5 g (4.39 mmoles) of 3-isobutoxyandrosta-3,5-dien-17-one were converted into 1.09 g (2.74 mmoles) of 3-isobutoxy-17$\beta$-hydroxy-17$\alpha$-pregna-3,5-diene-21-carboxylic acid $\gamma$-lactone showing a melting point of 130°–135° C. and IR absorptions (CHCl$_3$) of 1768, 1648, 1623, 1383 and 1167 cm$^{-1}$.

After hydrolysis, according to the procedure of Example VIII, 17$\beta$-hydroxy-3-oxo-17$\alpha$-pregn-4-ene-21-carboxylic acid $\gamma$-lactone was obtained.

EXAMPLE XIV

Following the procedure of Example VI 1.5 g (4.38 mmoles) of 3-butoxyandrosta-3,5-dien-17-one were converted into 3-butoxy-17$\beta$-hydroxy-17$\alpha$-pregna-3,5-diene-21-carboxylic acid $\gamma$-lactone which, after crystallisation from methanol, resulted in 0.80 g (2.00 mmoles) of the purified product showing a melting point of 123°–127° C. and IR absorptions (CHCl$_3$) of 1763, 1650, 1625 and 1169 cm$^{-1}$.

After hydrolysis, according to the procedure of Example VIII, 17$\beta$-hydroxy-3-oxo-17$\alpha$-pregn-4-ene-21-carboxylic acid $\gamma$-lactone was obtained.

EXAMPLE XV

Following the procedure of Example VI 1.5 g (4.57 mmoles) of 3-propoxyandrosta-3,5-dien-17-one were converted into 0.85 g (2.23 mmoles) of 3-propoxy-17$\beta$-hydroxy-17$\alpha$-pregna-3,5-diene-21-carboxylic acid $\gamma$-lactone showing a melting point of 132°–136° C. and IR absorptions (CHCl$_3$) of 1762, 1651, 1624 and 1168 cm$^{-1}$.

After hydriolysis, according to the procedure of Example VIII, 17$\beta$-hydroxy-3-oxo-17$\alpha$-pregn-4-ene-21-carboxylic acid $\gamma$-lactone was obtained.

EXAMPLE XVI

Following the procedure of Example VIII 2.1 g (6.33 mmoles) of 3$\beta$-methoxymethoxyandrost-5-en-17-one was converted into 1.06 g (2.73 mmoles) of 3$\beta$-methoxymethoxy-17$\beta$-hydroxy-17$\alpha$-pregn-5-ene-21-carboxylic acid $\gamma$-lactone showing, after crystallisation from a mixture of methylene chloride and heptane, a melting point of 157.5°–159° C. and IR absorptions (CHCl$_3$) of about 1763, about 1660, 1149, 1103, 1041, 1030 and 1020 cm$^{-1}$.

After hydrolysis, according to the procedure of Example VIII, and conversion according to the procedure of Example VII b, 17$\beta$-hydroxy-3-oxo-17$\alpha$-pregn-4-ene-21-carboxylic acid $\gamma$-lactone was obtained.

EXAMPLE XVII (a) Under a constant stream of nitrogen gas a solution of 15 ml of an 1.5 M n-butyllithium solution in hexane, diluted with 5 ml of tetrahydrofuran, was cooled to −60° C. Within 10 minutes a solution of 2 g (12 mmoles) of allyl dimethyl phosphate in 4.5 ml of toluene was added dropwise and the mixture was stirred for another 7 minutes at −65° C. After this, 1.8 g. (6 mimoles) of 3-methoxy-androsta-3,5-dien-17-one was added and the reaction mixture was stirred for 60 minutes at −65° C.

The reaction mixture was quenched with water and recovered in the same way as described in the foregoing examples, yielding 1.16 g (54%) of crystalline 3-methoxy-17β-hydroxy-17α-pregna-3,5-diene-21-carboxylic acid γ-lactone. After hydrolysis, according to the procedure of Example VIII, 17β-hydroxy-3-oxo-17α-pregn-4-ene-21-carboxylic acid γ-lactone was obtained.

(b) In the same way as described in (a) the following allyl phosphates were used:

(1) allyl diisopropyl phosphate, yielding 36% of the γ-lactone;

(2) allyl di-n-butyl phosphate, yielding 19% of the γ-lactone.

EXAMPLE XVIII (a) Within 30 minutes a solution of 60 g of allyl phosphate bis-di-n-butylamide in 60 ml of tetrahydrofuran was added dropwise to 147 ml of 2.5 M n-butyllithium in toluene at −40° C. Stirring was continued at this temperature for another 60 minutes and 26 g of 3-methoxy-androsta-3,5-dien-17-one were added. After an hour the reaction mixture was diluted with 500 ml of methylene chloride.

The solution obtained contained, according to HPLC, 14.4 g. (45%) of 3-methoxy-17β-hydroxy-17α-pregna-3,5-diene-21-carboxylic acid γlactone. 17β-Hydroxy-3-oxo-17α-pregn-4-ene-21-carboxylic acid γ-lactone was prepared therefrom according to the method of Example VIIb.

(b) In the same way as described in (a) the following allyl phosphate amides were used:

(1) allyl phosphate bis-morpholide; recovery in the usual way with water and organic solvent yielded 0.64 g of crystalline 3-methoxy-17β-hydroxy-17α-pregna-3,5-diene-21-carboxylic acid γ-lactone;

(2) allyl bis-(1-pyrrolidinyl) phosphate; thin layer chromatography analysis of the reaction mixture showed the presence of the γ-lactone.

EXAMPLE XIX (a) After cooling 10 ml. solution of 0.6 M vinyllithium in tetrahydrofuran, a solution of 0.77 g (3.1 mmoles) of allyl phosphate diethylamide in 4 ml of tetrahydrofuran was added dropwise thereto at −40° to −50° C. After stirring for 15 minutes at −45° C. a solution of 450 mg (1.5 mmoles) of 3-methoxy-androsta-3,5-dien-17-one in 4 ml of tetrahydrofuran was added, whereafter stirring was continued. According to thin layer chromatography some 3-methoxy-17β-hydroxy-17α-pregna-3,5-diene-21-carboxylic acid γ-lactone was detected.

17β-Hydroxy-3-oxo-17α-pregn-4-ene-21-carboxylic acid γ-lactone was prepared therefrom according to the method of Example VIIIb.

(b) In the same way as described in (a) a 0.4 M solution of phenyllithium in tetrahydrofuran was used. Inspection of the reaction mixture by thin layer chromatography showed the presence of the γ-lactone.

EXAMPLE XX (a) The procedure of Example XIX (a) was repeated, using t-butyllithium (1.95 M) dissolved in pentane, and added to the allyl phosphate bis-diethylamide solution in a short time at 0° C. The reaction mixture was cooled to −30° C. and was stirred for 15 minutes. A solution of 900 mg (3 mmoles) of 3-methoxy-androsta-3,5-dien-17-one in 10 ml of tetrahydrofuran was added at −40° C. After the usual recovery the toluene extract was concentrated, diluted with acetone and hydrolysed with p-toluenesulphonic acid and water. Column chromatography of the hydrolysis product yielded 25% of 17β-hydroxy-3-oxo-17α-pregn-4-ene-21-carboxylic acid γ-lactone.

(b) The same procedure as described in Example XIX (a) was followed, starting with 560 ml of a 2.2 M solution of n-butyllithium in cyclohexane and 160 g of allyl phosphate bis-diethylamide in 100 ml of tetrahydrofuran. After reaction and recovery the γ-lactone was obtained in a yield of 74%.

EXAMPLE XXI (a) A solution of 32 g of allyl phosphate bis-diethylamide in tetrahydrofuran was added slowly to a solution of n-butyllithium in toluene (98 ml, 2.5 M) at a temperature of +10° C. Stirring was continued for 2½ hours at +10° C. and 26 g of 3-methoxy-androsta-3,5-dien-17-one were added. The mixture was stirred for an hour at +10° C. and after addition of water and organic solvent the γ-lactone was isolated in a yield of 52%.

17β-Hydroxy-3-oxo-17α-pregn-4-ene-21-carboxylic acid γ-lactone was prepared therefrom according to the method of Example VIIb.

(b) In the way as described in (a) the reaction was carried out at +50° C. instead of +10° C. The reaction time of n-butyllithium and allyl phosphate bis-diethylamide was one hour, the reaction time of the steroid was 30 minutes only. The yield was 12% of the γ-lactone.

What we claim and desire to secure by letters patent is:

1. A process for the preparation of 17β-hydroxy-3-oxo-17α-pregn-4-ene-21-carboxylic acid γ-lactone and 17β-hydroxy-3-oxo-17α-pregna-4,6-diene-21-carboxylic acid γ-lactone of the formula:

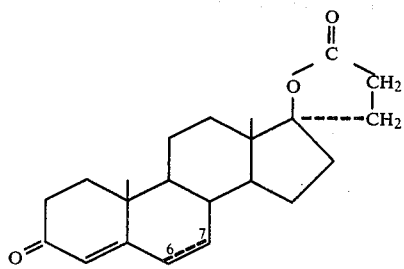

wherein the dotted line between the 6-7 positions indicates an optional double bond, the double bond being present in the latter compound, which comprises reacting an androst-5-ene-17-one of the formula:

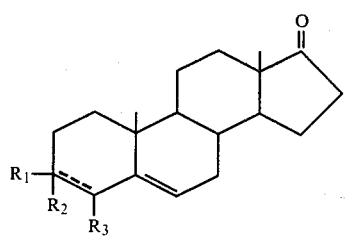

wherein:

(i) R₁ represents a group —OR₄, in which R₄ represents a hydrogen atom, an alkyl or methoxyalkyl group or a 2-tetrahydropyranyl group or a 2-tetrahydrofuryl group, and R₂ and R₃ each represent a hydrogen atom; or (ii) R₁ and R₂ are the same or different and each represents an alkoxy group or R₁ and R₂ together represent an alkylenedioxy group having 2 or 3 carbon atoms in the alkylene moiety, and R₃ represents a hydrogen atom, or (iii) R₁ represents an alkoxy or methoxyalkoxy group or a group $$-N\begin{matrix}R_7\\R_8\end{matrix}$$

wherein R₇ and R₈ are the same or different and each represents an alkyl group, or R₇ and R₈ together with the nitrogen atom to which they are attached represent a 5- or 6-membered heterocyclic group, which may contain a further hetero atom in the ring, and R₂ and R₃ together represent an additional bond in the 3–4 position with an organo-phosphorus compound of the formula:

$$\begin{matrix}R & O\\ & \parallel\\ & P-O-CH_2-CH=CH_2\\R & \end{matrix}$$ IV wherein:

R represents a group —OR' in which R' represents an alkyl group, or

R represents a group —N(R")₂ in which R" represents an alkyl group or —N(R")₂ represents a 5- or 6-membered heterocyclic group, which may contain a further hetero atom in the ring, wherein alkyl moieties in all of said formulas contain no more than 6 carbon atoms, in an organic medium at a temperature between about —90° and +50° C. in the presence of a strong base to obtain a corresponding γ-lactone of the formula:

V wherein R₁, R₂ and R₃ are as hereinbefore defined, and converting the compound thus obtained into the 3-oxo-pregn-4-ene-21-carboxylic acid γ-lactone or 3-oxo-pregna-4,6-diene-21-carboxylic acid γ-lactone of formula I.

2. A process according to claim 1, wherein the androst-5-ene-17-one of formula III is 3-methoxy- or 3-ethoxy-,3-propoxy or 3-butoxy-androsta-3,5-dien-17-one, 3β-(2'-tetrahydropyranyloxy)androst-5-en-17-one, 3,3-ethylenedioxy-androst-5-en-17-one, 3-(1'-pyrrolidinyl)-androsta-3,5-dien-17-one or 3-(n-morpholinyl)-androsta-3,5-dien-17-one.

3. A process according to claim 1, wherein the organophosphorus compound of formula IV is allyl phosphate bis-dimethyl- or bis-diethylamide or allyl dimethyl- or diethylphosphate.

4. A process according to claim 2, wherein the organophosphorus compound of formula IV is allyl phosphate bis-di-methyl- or -bis-diethylamide or allyl dimethyl- or diethylphosphate.

5. A process according to claim 1, 2, 3, or 4 wherein the reaction between the androstenone of formula III and the organophosphorus compound of formula IV is carried out in an organic medium.

6. A process according to claim 5, wherein the organic medium is a solvent selected from the group consisting of ethers, aromatic and aliphatic hydrocarbons and tertiary amines.

7. A process according to claim 6, wherein the organic medium is a solvent selected from the group consisting of tetrahydrofuran, diethyl ether, 1,2-dimethoxyethane, dioxane, benzene, toluene, xylene, naphthalene, pentane, hexane, cyclohexane, triethylamine and mixtures thereof.

8. A process according to claims 1, 2, 3 or 4 wherein the reaction is carried out at a temperature between —70° C. and 0° C.

9. A process according to claims 1,2,3 or 4 wherein the strong base is selected from the group consisting of alkyl- and aryl-lithium compounds.

10. A process according to claim 9, wherein the lithium compound is selected from the group consisting of n-butyllithium, t-butyllithium, methyllithium and phenyllithium.

11. A process according to claims 1,2,3 or 4 wherein the product is 17β-hydroxy-3-oxo-17α-pregn-4-ene-21-carboxylic acid γ-lactone.

12. A process according to claims 1,2,3 or 4 wherein the product is 17β-hydroxy-3-oxo-17α-pregna-4,6-diene-21-carboxylic acid γ-lactone.

13. A process according to claim 1 in which R₁ represents said alkoxy group and R₂ and R₃ together represent an additional bond in the 3–4 position.

14. A process according to claim 1 or 13 in which each of said alkoxy groups is a methoxy or ethoxy group.

* * * * *